United States Patent [19]

Stäb et al.

[11] Patent Number: 5,620,680
[45] Date of Patent: Apr. 15, 1997

[54] COSMETIC AND DERMATOLOGICAL LIGHT PROTECTION FORMULATIONS HAVING AN ACTIVE CONTENT OF CIS-UROCANINIC ACID

[75] Inventors: Franz Stäb, Echem; Gerhard Sauermann, Wiemersdorf; Beate Uhlmann, Hamburg, all of Germany

[73] Assignee: Beiersdorf Aktiengesellschaft, Hamburg, Germany

[21] Appl. No.: 115,528

[22] Filed: Sep. 2, 1993

[30] Foreign Application Priority Data

Sep. 9, 1992 [DE] Germany ............... 42 30 076.2

[51] Int. Cl.⁶ ............... A61K 7/42; A61K 31/415
[52] U.S. Cl. ............... 424/59; 424/60; 424/70.1; 514/400; 514/938
[58] Field of Search ............... 424/60, 59, 70.1; 514/938, 400

[56] References Cited

U.S. PATENT DOCUMENTS 4,181,804  1/1980  Mecca ............... 424/59
4,419,343  12/1983  Pauly ............... 424/59

OTHER PUBLICATIONS

Chemical Abstracts, vol. 72:43681, (abstract of French Patent 155992)(Jan. 31 1969), 1970, Canti.

Chemical Abstracts, vol.92:185715, (Japanese SCCJ (1979), vol. 13(2), pp. 61–66, 1980, Shigeki et al.

Derwent Abstract of German 4,121,030, Jan. 2, 1992, Engel.

*Primary Examiner*—Shelley A. Dodson
*Attorney, Agent, or Firm*—Sprung Horn Kramer & Woods

[57] ABSTRACT

The use of an active amount of cis-urocaninic acid as a light protection agent and/or antioxidant, if appropriate in a suitable galenic carrier, for cosmetic and/or dermatological purposes, the use of an active content of cis-urocaninic acid as a light protection agent and/or antioxidant in cosmetic and dermatological formulations, and the use of a mixture of cis- and trans-urocaninic acid as a light protection agent or antioxidant in cosmetic and dermatological formulations, wherein it must be ensured that at least the cis-urocaninic acid is present in an active concentration.

13 Claims, No Drawings

COSMETIC AND DERMATOLOGICAL LIGHT PROTECTION FORMULATIONS HAVING AN ACTIVE CONTENT OF CIS-UROCANINIC ACID

The present invention relates to light protection agents, in particular skin-care cosmetic and dermatological light protection agents, and to cosmetic and dermatological formulations comprising such light protection agents. The invention also particularly relates to skin cleansing products comprising such light protection agents.

The damaging effect of the ultraviolet component of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or burns of greater or lesser severity.

The narrower range around 308 nm is stated as having the maximum erythema activity of sunlight.

Numerous compounds are known for protection against UVB radiation, these being derivatives of 3-benzylidenecamphor, of 4-aminobenzoic acid, of cinnamic acid, of salicylic acid, of benzophenone and also of 2-phenylbenzimidazole.

It is also important to have filter substances available for the range between about 320 nm and about 400 nm, the so-called UVA range, since its rays can also cause damage. Thus, it has been proved that UVA radiation causes damage to the elastic and collagenic fibres of connective tissue, which ages the skin prematurely, and that it is to be regarded as the cause of numerous phototoxic and photoallergic reactions. The harmful influence of UVB radiation can be intensified by UVA radiation.

Certain derivatives of dibenzoylmethane are therefore used for protection against rays in the UVA range, although the photostability of these derivatives (Int. J. Cosm. Science 10, 53 (1988)) is not adequate.

However, UV radiation can also lead to photochemical reactions, the photochemical reaction products intervening in skin metabolism.

Such photochemical reaction products are chiefly free radical compounds, for example hydroxy radicals. Undefined free radical photoproducts which are formed in the skin itself can also display uncontrolled secondary reactions because of their high reactivity. Singlet oxygen, an excited state of the oxygen molecule without free radicals, however, can also occur under UV irradiation, as can short-lived epoxides and many other compounds. Singlet oxygen is distinguished, for example, by an increased reactivity compared with the triplet oxygen usually present (free radical ground state). Nevertheless, excited, reactive (free radical) triplet states of the oxygen molecule also exist.

UV radiation is furthermore regarded as ionizing radiation. There is therefore the risk of ionic species also forming on exposure to UV, these species then in turn being capable of intervening oxidatively in biochemical processes.

In order to prevent these reactions, antioxidants and/or agents which trap free radicals can additionally be incorporated into cosmetic or dermatological formulations.

The compounds, some of which are mentioned above, which are employed as light protection agents for cosmetic and dermatological light protection formulations are distinguished by a good light protection action. However, they have the disadvantage that to date it has been difficult for them to be incorporated into such formulations in a satisfactory manner. Furthermore, these compounds are pure UV-absorbing agents and are unsuitable as agents which trap free radicals.

It has already been proposed to employ vitamin E, a substance having a known antioxidative action, in light protection formulations, but here also, the action achieved remains far below that hoped for.

It is also known to employ trans-urocaninic acid (also called trans-urocanic acid, E-urocaninic acid, E-urocanic acid, trans-(4-imidazolyl)acrylic acid or E-4-imidazolylacrylic acid) as light protection agents.

Examples are to be found in Japanese Published Specifications JP-Kokai-Sho-54/027562, JP-Kokai-Sho-63/051318 and JP-Kokai-Sho-56/063965 and in the associated laid-open specifications.

When urocaninic acid was referred to in connection with cosmetic or dermatological light protection, trans-urocaninic acid was always meant, even if the trans-configuration was not expressly mentioned. trans-Urocaninic acid is characterized by the following structural formula:

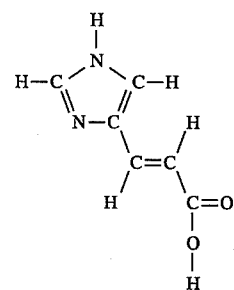

However, it was surprising and not to be foreseen by the expert that cosmetic and dermatological light protection formulations having an active content of cis-urocaninic acid remedy the disadvantages of the prior art.

cis-Urocaninic acid (also called cis-urocanic acid, Z-urocaninic acid, Z-urocanic acid, trans-(4-imidazolyl)acrylic acid or Z-4-imidazolylacrylic acid) is characterized by the following structural formula:

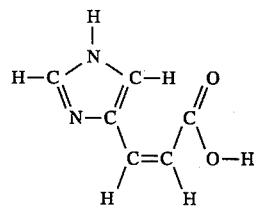

It has the empirical formula $C_6H_6N_2O_2$ and a molecular weight of 138.12. cis-Urocaninic acid is formed, for example, by UV irradiation of the trans isomer, which occurs in human skin and also in perspiration.

It was astonishing that cis-urocaninic acid would be active as a light protection agent, since its absorption maximum in vitro is between 270 and 280 nm, that is to say is significantly outside the range of interest for cosmetic or dermatological light protection.

However, it has been found that cis-urocaninic acid undergoes a shift in its absorption maximum in vivo, that is to say on human skin. On the skin, the most intense absorption maximum is at about 303–308 nm, and a further although significantly less intense absorption maximum lies at about 290 nm. The range of the most intense absorption, which includes the most intense absorption maximum, extends from about 295 to 335 nm, the absorption of cis-urocaninic acid on the skin over the entire wavelength range of about 300–320 nm being at least as intense as the most intense absorption maxima of trans-urocaninic acid at the same concentration.

cis-Urocaninic acid consequently can be regarded essentially as a UVB absorber, although it also still absorbs noticeably in the UVA range.

It was not to be foreseen that cis-urocaninic acid or the cosmetic or dermatological formulations according to the invention having an active content of cis-urocaninic acid would provide better protection against damage by UV radiation act better as an antioxidant act better as an agent which traps free radicals prevent bonding of harmful photoproducts to lipids, DNA and proteins to a better extent than the formulations of the prior art. Furthermore, it was not to be foreseen that cis-urocaninic acid or the cosmetic or dermatological formulations according to the invention having an active content of cis-urocaninic acid would have a sufficiently high stability for use lead to products tolerated by the skin not intervene in endogenous microorganism flora be available and active even in wash-active formulations, such as shampoos and shower formulations and the like increase the skin moisture content and compensate the washing out of endogenous urocaninic acid.

It was furthermore surprising that cis-urocaninic acid would also act as an antioxidant in photochemical oxidation processes relative to human skin. The anti-oxidative physiological action of cis-urocaninic acid—which is probably due to its property as an agent which traps free radicals—was not previously known.

It is indeed known from DE-OS 41 21 030 to add cis-urocaninic acid to dermatological formulations which exhibit various actions, including antipsoriatic and antiallergic actions and the like. However, at no point does this document suggest the advantageous properties of cis-urocaninic acid as a light protection agent and agent which traps free radicals.

The cosmetic and/or dermatological formulations and cis-urocaninic acid, which acts as a UV absorber, in particular a UVB absorber, are preferably used for protection of the skin and hair from UV rays, in particular UVB rays.

The cosmetic and/or dermatological formulations according to the invention can have the customary composition and be used in the customary manner for treatment, care and cleansing of skin and/or hair and as a make-up product in decorative cosmetics. They preferably comprise 0.01% by weight to 10% by weight, but in particular 0.1% by weight to 6% by weight, based on the total weight of the agent, of cis-urocaninic acid.

Nevertheless, reference is made to the appropriate legislation of individual states which specifies the maximum values for active compound concentrations in the individual case. In Germany, at the current point in time, the maximum concentration of urocaninic acid (cis- and trans-isomer together) is limited to 2.0% by weight, based on the total weight of the composition.

In formulations having a cis-urocaninic acid concentration of 2.0% by weight comprising no other light protection agent, light protection factors of the order of 2.5 to 3.5 can be achieved.

For use, the cosmetic and dermatological formulations according to the invention are applied to the skin and/or hair in an adequate amount in the manner customary for cosmetics.

Those cosmetic and dermatological formulations which are in the form of a sunscreen agent are particularly preferred. These preferably additionally comprise at least one UVA filter and/or at least one other UVB filter and/or at least one inorganic pigment.

Cosmetic and dermatological formulations according to the invention for protecting the skin from UV rays can be in various forms, such as are usually employed, for example, for this type of formulation. They can thus be, for example, a solution, an emulsion of the water-in-oil (W/O) type or of the oil-in-water (O/W) type, or a multiple emulsion, for example of the water-in-oil-in-water (W/O/W) type, a gel, a solid stick or also an aerosol.

It is also possible and advantageous in the context of the present invention to introduce cis-urocaninic acid into aqueous systems or surfactant formulations for cleansing of the skin and hair.

The cosmetic and dermatological formulations according to the invention can comprise cosmetic auxiliaries such as are usually used in such formulations, for example preservatives, bactericides, perfumes, substances for preventing foaming, dyestuffs, pigments which have a colouring action, thickening agents, surface-active substances, emulsifiers, softening, moistening and/or humectant substances, fats, oils, waxes or other customary constituents of a cosmetic or dermatological formulation, such as alcohols, polyols, polymers, foam stabilisers, electrolytes, organic solvents or silicone derivatives.

If the cosmetic or dermatological formulation is a solution or lotion, solvents which can be used are:

water or aqueous solutions;

oils, such as triglycerides of capric or of caprylic acid, but preferably castor oil;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. In the case of alcoholic solvents, water can be a further constituent.

Emulsions according to the invention, for example in the form of a sunscreen cream or a sunscreen milk, are preferred and comprise, for example, the fats, oils, waxes and other fatty substances mentioned, as well as water and an emulsifier, such as usually used for such a type of formulation.

Gels according to the invention usually comprise alcohols of low C number, for example ethanol, isopropanol, 1,2-propanediol or glycerol, and water or an abovementioned oil in the presence of a thickening agent, which is preferably silicone dioxide or an aluminium silicate in oily-alcoholic gels and preferably a polyacrylate in aqueous-alcoholic or alcoholic gels.

Solid sticks according to the invention comprise, for example, naturally occurring or synthetic waxes, fatty alcohols or fatty acid esters. Lip-care sticks are preferred.

Suitable propellants for cosmetic deodorants according to the invention which can be sprayed from aerosol containers are the customary known readily volatile, liquefied propellants, for example hydrocarbons (propane, butane or isobutane), which can be employed by themselves or as a mixture with one another. Compressed air can also advantageously be used.

The expert of course knows that there are nontoxic propellant gases per se which would be suitable in principle for the present invention, but which nevertheless should be dispensed with because of their unacceptable action on the environment or other concomitant circumstances, in particular fluorohydrocarbons and fluorochlorohydrocarbons (FCHCs).

The cosmetic or dermatological formulations for protection of the skin comprise compounds of the formula I, for example, in amounts of 0.1% by weight to 30% by weight, preferably in amounts of 0.5% by weight to 10% by weight, but in particular 1% by weight to 6% by weight, based on the total weight of the formulations.

They can preferably furthermore comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation. They can also be used as sunscreen agents.

The UVB filters can be oil-soluble or water-soluble. Oil-soluble substances which may be mentioned are, for examples:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxy cinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzylidenemalonic acid, preferably 2-ethylhexyl 4-methoxybenzylidenemalonate; and 2,4,6-trianilino-(p-carbo-2'-ethyl-1'-hexyloxy)-1,3,5-triazine.

Water-soluble substances which may be mentioned are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)sulphonic acid and their salts.

The list of UVB filters mentioned, which can be used in combination with the compounds of the general formula I, is of course not intended to be limiting.

The invention also relates to the combination of a UVA filter according to the invention with a UVB filter and to a cosmetic or dermatological formulation according to the invention which also comprises a UVB filter.

It may also be advantageous to combine cis-urocaninic acid with UVA filters which were hitherto usually contained in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations and to formulations comprising these combinations. The amounts used for the UVB combination can be employed.

Cosmetic and dermatological formulations having an active content of cis-urocaninic acid can also comprise inorganic pigments which are usually used in cosmetics for protection of the skin from UV rays. These are oxides of titanium, zinc, iron, zirconium, silicon, manganese, aluminium and cerium and mixtures thereof, as well as modifications in which the oxides are the active agents. They are particularly preferably pigments based on titanium dioxide. The invention also relates to these combinations of UVA filter and pigment and to formulations comprising this combination. The amounts mentioned for the above combinations can be used.

Cosmetic and dermatological formulations according to the invention for protection of the hair from UV rays are, for example, shampooing agents, formulations which are used when rinsing the hair before or after shampooing, before or after permanent wave treatment or before or after colouring or bleaching of the hair, formulations for blow-drying or setting hair, formulations for colouring or bleaching, a styling and treatment lotion, a hair spray or permanent wave agents. The cosmetic and dermatological formulations comprise active compounds and auxiliaries such as are usually used for this type of formulations for hair care and hair treatment. Auxiliaries which can be used are preservatives, surface-active substances, substances for preventing foaming, emulsifiers, thickening agents, fats, oils, waxes, organic solvents, bactericides, perfumes, dyestuffs or pigments, the task of which is to colour the hair or the cosmetic or dermatological formulation itself, electrolytes and substances against the hair becoming greasy.

Cosmetic formulations which are a skin cleansing agent or shampooing agent preferably comprise at least one anionic, non-ionic or amphoteric surface-active substance, or also mixtures of such substances, at least one compound of the general formula I in an aqueous medium, and auxiliaries such as are usually used for this purpose. The surface-active substance or the mixtures of these substances can be present in the shampooing agent in a concentration of between 1% by weight and 50% by weight.

If the cosmetic or dermatological formulations are in the form of a lotion which is rinsed out and is used, for example, before or after bleaching, before or after shampooing, between two shampooing steps or before or after permanent wave treatment, they are, for example, aqueous or aqueous-alcoholic solutions, which optionally comprise surface-active substances, preferably non-ionic or cationic surface-active substances, the concentration of which can be between 0.1 and 10% by weight, preferably between 0.2 and 5% by weight. These cosmetic or dermatological formulations can also be aerosols comprising the auxiliaries usually used for this purpose.

A cosmetic formulation in the form of a lotion which is not rinsed out, in particular a lotion for setting hair, a lotion used when blow-drying the hair or a styling and treatment lotion, is in general an aqueous, alcoholic or aqueous-alcoholic solution and comprises at least one cationic, anionic, non-ionic or amphoteric polymer or also mixtures thereof, as well as the cis-urocaninic acid in an active concentration. The amount of polymers used is, for example, between 0.1 and 10% by weight, preferably between 0.1 and 3% by weight.

Cosmetic formulations for treatment and care of hair which comprise at least one compound of the general formula I according to the invention can be in the form of emulsions which are of the non-ionic or anionic type. Non-ionic emulsions comprise, in addition to water, oils or fatty alcohols, which, for example, can also be polyethoxylated or polypropoxylated, or also mixtures of the two organic components. These emulsions optionally comprise cationic surface-active substances.

Cosmetic formulations for treatment and care of hair can be in the form of gels which, in addition to an active content of cis-urocaninic acid and the solvents usually used for this purpose, preferably water, can also comprise organic thickening agents, for example gum arabic, xanthan gum, sodium alginate or cellulose derivatives, preferably methylcellulose, hydroxymethylcellulose, hydroxyethylcellulose, hydroxypropylcellulose or hydroxypropylmethylcellulose, or inorganic thickening agents, for example aluminium silicates, such as, for example, bentonites, or a mixture of polyethylene glycol and polyethylene glycol stearate or distearate. The gel comprises the thickening agent, for example, in an amount of between 0.1 and 30% by weight, preferably between 0.5 and 15% by weight.

The amount of cis-urocaninic acid in an agent intended for hair is preferably 0.05% by weight to 10% by weight, in particular 0.5% by weight to 5% by weight, based on the total weight of the agent.

The present invention also relates to a method for protecting the skin and hair from UVA radiation, which is characterized in that a cosmetic agent which comprises an active concentration of cis-urocaninic acid is applied to the skin or hair in an adequate amount, and to the use of these compounds in particular for this purpose.

The present invention also relates to a process for protecting colourless or coloured cosmetic or dermatological formulations from UV rays, in particular UVB rays, and to these formulations, which are, for example, the abovementioned formulations for treatment and care of hair, in particular hair colouring agents, hair sprays, shampooing agents and colour shampooing agents, make-up products, such as, for example, nail varnishes, lipsticks, complexion foundations, washing and shower formulations and creams for treatment of the skin, or all other cosmetic agents, the constituents of which involve stability problems because of light during storage, characterized in that the cosmetic agents have an active content of cis-urocaninic acid.

The amount of cis-urocaninic acid in these formulations is preferably 0.01% by weight to 10% by weight, in particular 0.1% by weight to 3% by weight, based on the total weight of the formulations.

All the amounts data, contents and percentages are based on the weight and the total amount or on the total weight of the formulations, unless stated otherwise.

The invention also relates to the process for the preparation of the cosmetic agents according to the invention, which is characterized in that cis-urocaninic acid is incorporated into cosmetic and dermatological formulations in a manner which is known per se.

The following examples are intended to illustrate the present invention without limiting it. UCA in these examples always means cis-urocaninic acid. Examples 1–18 embody advantageous formulations which comprise cis-urocaninic acid as the sole substance which is active against UV radiation, and the remaining examples are combinations of cis-urocaninic acid with other substances which protect against UV radiation.

EXAMPLE 1

Aqueous Formulation (Face Lotion)

|  | % by weight |
| --- | --- |
| PEG 40-hydrogenated castor oil | 0.811 |
| Dipropylene glycol | 2.534 |
| PEG 8 | 1.521 |
| Na$_3$EDTA | 0.253 |
| Polymer JR 125 | 0.025 |
| UCA | 0.750 |
| Water DEM | to 100.000 |

EXAMPLE 2

Aqueous Composition

|  | % by weight |
| --- | --- |
| Poly-fatty acid ester (Cetiol HE) | 16.000 |
| PPG 3-myristyl ether (Witconol APM) | 1.000 |
| Propylene glycol | 3.000 |
| Glycerol | 40.000 |
| UCA | 0.500 |
| Water DEM | to 100.000 |

EXAMPLE 3

Hydrogel (Polyacrylate Gel)

|  | % by weight |
| --- | --- |
| Acrylic acid polymer (Carbopol 934) | 1.000 |
| Tris(hydroxymethylamino)methane (Tris) | 1.000 |
| Glycerol | 2.000 |
| Propylene glycol | 2.000 |
| UCA | 0.050 |
| Water DEM | to 100.000 |

EXAMPLE 4

Formulation of High Water Content (Very Soft)

|  | % by weight |
| --- | --- |
| Ceteareth (Cremophor A 25) | 0.100 |
| Cetearyl alcohol (Lanette O) | 0.400 |
| Vaseline, GP 9 | 12.500 |
| Mineral oil, GP 9 | 11.000 |
| Ceteareth 6-stearyl alcohol (Cremophor A6) | 6.000 |
| UCA | 0.020 |
| Water DEM | to 100.000 |

EXAMPLE 5

Formulation of High Water Content (Soft)

|  | % by weight |
| --- | --- |
| Ceteareth-25 (Cremophor A25) | 1.500 |
| Cetearyl alcohol (Lanette O) | 8.500 |

EXAMPLE 6

Formulation of High Water Content (Soft)

|  | % by weight |
|---|---|
| UCA | 0.250 |
| Water DEM | to 100.000 |

| | % by weight |
|---|---|
| Ceteareth-25 (Cremophor A25) | 2.000 |
| Cetearyl alcohol (Lanette O) | 8.000 |
| Vaseline, GP 9 | 10.000 |
| Mineral oil, GP 9 | 10.000 |
| UCA | 0.100 |
| Water DEM | to 100.000 |

EXAMPLE 7

Formulation of High Water Content (Semi-Solid)

| | % by weight |
|---|---|
| Ceteareth-25 | 3.000 |
| Cetearyl alcohol (Lanette O) | 17.000 |
| UCA | 0.175 |
| Water DEM | to 100.000 |

EXAMPLE 8

Thinly Mobile Lotion

| | % by weight |
|---|---|
| Ceteareth-25 (Cremophor A25) | 1.000 |
| Ceteareth 6-stearyl alcohol (Cremophor A6) | 1.000 |
| Glycerol mono-distearate (Tegin normal) | 2.000 |
| Cetyl alcohol | 1.000 |
| Isopropyl myristate | 1.450 |
| Glycerol | 1.000 |
| Polyvinylpyrrolidone | 0.500 |
| UCA | 0.129 |
| Water DEM | to 100.000 |

EXAMPLE 9

Viscous Lotion

| | % by weight |
|---|---|
| Ceteareth 25 (Cremophor A25) | 2.000 |
| Cetearyl alcohol (Lanette O) | 3.000 |
| Mineral oil, GP 9 | 5.000 |
| Propylene glycol | 3.000 |
| Polyvinylpyrrolidone | 0.500 |
| UCA | 0.300 |
| Water DEM | to 100.000 |

EXAMPLE 10

W/O Cream

| | % by weight |
|---|---|
| Glycerol sorbitan fatty acid ester (Arlacel 481) | 6.000 |
| Microcrystalline wax (Lunacera M) | 1.000 |
| Neutral oil | 3.000 |
| Paraffin oil | 19.000 |
| Magnesium stearate | 1.000 |
| Propylene glycol | 3.700 |
| Magnesium sulphate ($MgSO_4 \cdot 7 H_2O$) | 0.700 |
| UCA | 1.000 |
| Water DEM | to 100.000 |

EXAMPLE 11

W/O Emulsion

| | % by weight |
|---|---|
| Polyoxyethylene glycerol sorbitan fatty acid ester (Arlacel 988) | 3.600 |
| Polyoxyethylene fatty acid ester (Arlacel 989) | 1.400 |
| Cetearyl alcohol (Lanette O) | 2.000 |
| Mineral oil, GP 9 | 25.000 |
| Paraben mixture | as required |
| Magnesium sulphate ($MgSO_4 \cdot 7 H_2O$) | 0.700 |
| UCA | 1.250 |
| Water DEM | to 100.000 |

EXAMPLE 12

W/O Lotion

| | % by weight |
|---|---|
| Glycerol sorbitan fatty acid ester (Arlacel 481) | 1.300 |
| Polyoxyethylene fatty acid ester (Arlacel 989) | 3.700 |
| Neutral oil (Miglyol) | 6.000 |
| Paraffin oil, GP 9 | 14.000 |
| Propylene glycol | 3.800 |
| Magnesium sulphate ($MgSO_4 \cdot 7 H_2O$) | 0.700 |
| UCA | 0.060 |
| Water DEM | to 100.000 |

EXAMPLE 13

O/W Emulsion % by Weight

| | % by weight |
|---|---|
| PEG 100-stearate (Arlacel 165) | 5.000 |
| Cetearyl alcohol (Lanette O) | 3.000 |
| Mineral oil, GP 9 | 25.000 |
| Paraben mixture | as required |
| UCA | 0.325 |
| Water DEM | to 100.000 |

EXAMPLE 14

O/W Emulsion

|  | % by weight |
|---|---|
| Polysorbate 60 (Tween 60) | 3.000 |
| Sorbitan stearate (Arlacel 60) | 2.000 |
| Cetearyl alcohol (Lanette O) | 3.000 |
| Mineral oil, GP 9 | 25.000 |
| Paraben mixture | as required |
| UCA | 0.035 |
| Water DEM | to 100.000 |

EXAMPLE 15

Cationic Emulsion

|  | % by weight |
|---|---|
| Distearyldimethylammonium chloride (Genamin DS AC) | 5.000 |
| Vaseline, GP 9 | 5.000 |
| Isopropyl palmitate | 2.000 |
| Cetyl alcohol | 1.000 |
| Silicone oil | 0.100 |
| Propylparaben | 0.100 |
| Methylparaben | 0.100 |
| Glycerol | 4.000 |
| UCA | 0.090 |
| Water DEM | to 100.000 |

EXAMPLE 16

Ionic Emulsion

|  | % by weight |
|---|---|
| Sodium cetearyl sulphate (Emulgade F) | 6.000 |
| Mineral oil, GP 9 | 25.000 |
| Paraben mixture | as required |
| UCA | 0.450 |
| Water DEM | to 100.000 |

EXAMPLE 17

Ionic O/W Emulsion

|  | % by weight |
|---|---|
| Stearic acid | 5.000 |
| Cetearyl alcohol (Lanette O) | 3.000 |
| Mineral oil, GP 9 | 25.000 |
| Paraben mixture | as required |
| Triethanolamine | 1.000 |
| UCA | 0.080 |
| Water DEM | to 100.000 |

EXAMPLE 18

Sun Oil

| | |
|---|---|
| UCA | 30.0 g |
| 3-(4'-Methylbenzylidene)camphor ("Eusolex 6300", Merck) | 60.0 g |
| Myristyl alcohol, polyoxypropylated with 3 mol of propylene oxide ("Witconol APM", Witco) | 608.0 g |
| $C_{12}$—$C_{15}$-alcohol benzoate ("Finsolv TN", Witco) | 152.0 g |
| Glycerol monococoate, polyoxyethylated with 7 mol of ethylene oxide ("Cetiol HE", Henkel KGaA) | 100.0 g |
| Ethanol | 65.0 g |
| 2-Octadodecanol | 20.0 g |
| Perfume, correctants, additives, antioxidants, stabilisers | as required |

The constituents of the sun oil are mixed with one another and at the same time heated, if appropriate, to 40° to 50° C. for homogenisation.

EXAMPLE 19

Sun Gel

| | |
|---|---|
| UCA | 18.0 g |
| 2,4,6-Trianilino-(p-carbo-2'-ethylhexyl-1'-oxy)-1,3,5-triazin ("Uvinul" T-150, BASF) | 25.0 g |
| Isopropyl myristate | 189.0 g |
| $C_{12}$—$C_{15}$-alcohol benzoate ("Finsolv TN", Witco) | 76.0 g |
| Myristyl alcohol, polyoxypropylated with 3 mol of propylene oxide ("Witconol APM", Witco) | 304.0 g |
| Caprylic/capric acid triglyceride ("Miglyol neutral oil", Dynamit-Nobel) | 195.0 g |
| "Bentone-38", Kronos-Titan | 150.0 g |
| Propylene carbonate | 20.0 g |
| Ethanol | 23.0 g |
| Perfume, correctants, additives, antioxidants, stabilisers | as required |

A sun gel is prepared with the constituents mentioned in the customary manner.

EXAMPLE 20

Hydrogel

| | |
|---|---|
| UCA | 15.0 g |
| 2-Phenylbenzimidazole-5-sulphonic acid ("Eusolex 232", Merck) | 27.0 g |
| Allantoin | 2.0 g |
| Liquid sorbitol ("Karion F", Merck) | 22.0 g |
| "Carbopol 934", B. F. Goodrich | 15.0 g |
| Tris(hydroxymethyl)aminomethane | 27.0 g |
| Propylene glycol | 10.0 g |
| Ethanol | 300.0 g |
| Water | 582.0 g |
| Perfume, correctants, additives, antioxidants, stabilisers | as required |

A hydrogel is prepared with the constituents mentioned in the customary manner.

EXAMPLE 21

Oil-in-Water Emulsion (Sun Cream)

| | |
|---|---|
| UCA | 20.0 g |
| 2-Phenylbenzimidazole-5-sulphonic acid ("Eusolex 232", Merck) | 32.0 g |
| Stearyl alcohol oxyethylated with 2 mol of ethylene oxide ("Brij 72", ICI) | 30.0 g |
| Stearyl alcohol oxyethylated with 21 mol of | 20.0 g |

-continued

| | |
|---|---|
| ethylene oxide ("Brij 721", ICI) | |
| Cetyl stearyl alcohol | 25.0 g |
| Myristyl alcohol, polyoxypropylated with 3 mol of propylene oxide ("Witconol APM", Witco) | 64.0 g |
| $C_{12}$—$C_{15}$-alcohol benzoate ("Finsolv TN", Witco) | 16.0 g |
| Propylene glycol | 35.0 g |
| Tris(hydroxymethyl)aminomethane | 14.0 g |
| Water | 744.0 g |
| Perfume, correctants, additives, antioxidants, stabilisers | as required |

The fatty substances are heated to 80° to 85° C. The water-soluble constituents, including the cis-urocaninic acid, are dissolved in water at the same temperature, the two phases are mixed with one another, with vigorous stirring, and the mixture is allowed to cool, with moderate stirring.

EXAMPLE 22

Oil-in-Water Emulsion (Sun Cream)

| | |
|---|---|
| UCA | 33.0 g |
| 2,4,6-Trianilino-(p-carbo-2'-ethylhexyl-1'-oxy)-1,3,5-triazine ("Uvinul T-150", BASF) | 18.0 g |
| $C_{12}$—$C_{15}$-alcohol benzoate ("Finsolv TN", Witco) | 47.0 g |
| Cetyl stearyl alcohol | 30.0 g |
| Mixture of the stearic acid mono- and diester of glycerol, and the stearic acid ester of polyethylene oxide ("Arlacel 165", ICI) | 50.0 g |
| Myristyl alcohol, polyoxypropylated with 3 mol of propylene oxide ("Witconol APM", Witco) | 185.0 g |
| Water | 637.0 g |
| Perfume, correctants, additives, antioxidants, stabilisers | as required |

The emulsion is prepared in accordance with the above example.

EXAMPLE 23

Water-in-Oil Emulsion (Sunscreen Milk)

| | |
|---|---|
| UCA | 20.0 g |
| 1-(4'-tert-Butylphenyl)-3-(4'-methoxyphenyl)-propane-1,3-dione ("Parsol 1789", Givaudan) | 15.0 g |
| 2'-Ethylhexyl 4-methoxycinnamate ("Parsol MCX", Givaudan) | 35.0 g |
| Ester of saturated fatty acids with polyethylene oxide ("Arlacel 989", ICI) | 37.0 g |
| Ester of unsaturated fatty acids with glycerol and sorbitan ("Arlacel 481", ICI) | 13.0 g |
| Myristyl alcohol, polyoxypropylated with 3 mol of propylene oxide ("Witconol APM", Witco) | 160.0 g |
| $C_{12}$—$C_{15}$-alcohol benzoate ("Finsolv TN", Witco) | 40.0 g |
| Magnesium sulphate heptahydrate | 7.0 g |
| Water | 673.0 g |
| Perfume, correctants, additives, antioxidants, stabilisers | as required |

The emulsion is prepared in a manner corresponding to that described under Example 21.

EXAMPLE 24

Water-in-Oil Emulsion (Sunscreen Milk)

| | |
|---|---|
| UCA | 15.0 g |
| 2-Ethylhexyl 4-methoxycinnamate ("Parsol MCX", Givaudan) | 15.0 g |
| 3-(4'-Methylbenzylidene)camphor ("Eusolex 6300", Merck) | 3.0 g |
| Ester of unsaturated fatty acids with glycerol and sorbitan ("Arlacel 481", ICI) | 60.0 g |
| Microwax ("Lunacera 11", Fuller) | 10.0 g |
| Caprylic/capric acid triglyceride ("Miglyol neutral oil", Dynamit-Nobel) | 20.0 g |
| Myristyl alcohol, polyoxypropylated with 3 mol of propylene oxide ("Witconol APM", Witco) | 145.0 g |
| $C_{12}$—$C_{15}$-alcohol benzoate ("Finsolv TN", Witco) | 37.0 g |
| Magnesium stearate | 10.0 g |
| Propylene glycol | 37.0 g |
| Magnesium heptahydrate | 7.0 g |
| Water | 641.0 g |
| Perfume, correctants, additives, antioxidants, stabilisers | as required |

The emulsion is prepared in a manner corresponding to that described under Example 21.

EXAMPLE 25

Water-in-Oil Emulsion (Sunscreen Milk)

| | |
|---|---|
| UCA | 33.0 g |
| 2-Ethylhexyl 4-methoxycinnamate ("Parsol MCX", Givaudan) | 15.0 g |
| 3-(4'-Methylbenzylidene)camphor ("Eusolex 6300", Merck) | 3.0 g |
| Ester of unsaturated fatty acids with glycerol and sorbitan ("Arlacel 481", ICI) | 60.0 g |
| Microwax ("Lunacera 11", Fuller) | 10.0 g |
| Caprylic/capric acid triglyceride ("Miglyol neutral oil", Dynamit-Nobel) | 20.0 g |
| Myristyl alcohol, polyoxypropylated with 3 mol of propylene oxide ("Witconol APM", Witco) | 119.0 g |
| $C_{12}$—$C_{15}$-alcohol benzoate ("Finsolv TN", Witco) | 30.0 g |
| Magnesium stearate | 10.0 g |
| Propylene glycol | 37.0 g |
| Magnesium sulphate heptahydrate | 7.0 g |
| Water | 656.0 g |
| Perfume, correctants, additives, antioxidants, stabilisers | as required |

The emulsion is prepared in a manner corresponding to that described under Example 21.

EXAMPLE 26

Cationic Emulsion for Rinsing Hair

| | |
|---|---|
| UCA | 2.0 g |
| Dimethyldistearylammonium chloride ("Arosorf TA 100", Rewo) | 50.0 g |
| Vaseline | 50.0 g |
| Isopropyl palmitate | 20.0 g |
| Cetyl alcohol | 10.0 g |
| Water | 864.0 g |
| Glycerol | 4.0 g |
| Perfume, correctants, additives, antioxidants, stabilisers | as required |

A hair rinsing agent is prepared with the constituents mentioned in the customary manner.

To prepare the cosmetic agent, the cis-urocaninic acid is dissolved in the aqueous phase and the oil-soluble UV filter is dissolved in the fatty phase. In the above Examples 22, 23, 25, 29 and 30, the oil-soluble UV filter according to the invention is dissolved in the fatty phase, and in Examples 24, 26, 27, 28 and 31 the cis-urocaninic acid is dissolved in the aqueous phase.

We claim:

1. In a cosmetic or dermatological composition comprising a galenic carrier, an active material and a light protection agent or antioxidant, the improvement wherein said light protection agent or antioxidant comprises an effective amount of cis-urocaninic acid.

2. A composition according to claim 1, wherein the cis-urocaninic acid is present in from 0.01 to 10% by weight.

3. A composition according to claim 1, wherein the cis-urocaninic acid is present in from 0.1 to 6% by weight.

4. A composition according to claim 1, in the form of a solution or lotion, an emulsion, an oily-alcoholic or aqueous-alcoholic or alcoholic gel, a stick or an aerosol.

5. A composition according to claim 1 containing at least one member selected from the group consisting of preservatives, bactericides, perfumes, agents for preventing foaming, dyestuffs, pigments which have a coloring action, thickening agents, surface-active agents, emulsifiers, softening agents, moistening agents, humectant agents, fats, oils, waxes, alcohols, polyols, polymers, foam stabilizers, electrolytes, organic solvents and silicone derivatives.

6. A composition according to claim 1, additionally containing at least one member selected from the group consisting of a UVB filter, UVA filter and an inorganic pigment.

7. A composition according to claim 1, additionally containing at least one UVB filter selected from the group consisting of 3-benzylidenecamphor derivatives, 4-aminobenzoic acid derivatives, esters of cinnamic acid, esters of salicylic acid, derivatives of benzophenone, esters of benzalmalonic acid, 2,4,6-trianilino-(p-carbo-2'-ethyl-1'-hexyloxy)-1,3,5-triazine, salts of 2-phenylbenzimidazole-5-sulphonic acid, sulphonic acid derivatives of benzo-phenones and sulphonic acid derivatives of 3-benzylidenecamphor.

8. A composition according to claim 1, additionally containing at least one UVA filter selected from the group consisting of a derivative of dibenzoyl-methane, 1-(4'-tert-butylphenyl) -3-(4'-methoxyphenyl)-propane-1,3-dione or 1-phenyl-3-(4'-isopropylphenyl)-propane-1,3-dione.

9. A composition according to claim 1, containing a titanium dioxide-based pigment.

10. A composition according to claim 1, which is a member selected from the group consisting of a shampooing agent, a washing or shower formulation, a lotion, a gel or an emulsion for rinsing, a styling or treatment lotion or a corresponding gel, a lotion or a gel for blow-drying or for setting hair, a hair spray, a permanent wave treatment agent and an agent for bleaching or coloring.

11. A composition according to claim 1, further containing at least one auxiliary selected from the group consisting of surface-active agents, thickening agents, polymers, preservatives, foam stabilizers, electrolytes, organic solvents, silicone derivatives, oils, waxes, dyestuffs and pigments.

12. A composition according to claim 1, wherein the active material is a hair treatment agent or a make-up product.

13. In the protection of skin and hair by applying thereto an active material and a light protection agent or antioxidant, the improvement wherein said light protection agent or antioxidant comprises an effective amount of cis-urocaninic acid, optionally admixed with trans-urocaninic acid.

* * * * *